US008667961B2

(12) United States Patent
Thoemmes et al.

(10) Patent No.: US 8,667,961 B2
(45) Date of Patent: Mar. 11, 2014

(54) INHALER FOR DELIVERY OF A POWDER FORMULATION FROM A BLISTER STRIP

(71) Applicant: Boehringer Ingelheim International GmbH, Ingelheim am Rhein (DE)

(72) Inventors: Ralf Thoemmes, Ingelheim am Rhein (DE); Jessica Frentzel-Beyme, Ingelheim am Rhein (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/754,024

(22) Filed: Jan. 30, 2013

(65) Prior Publication Data

US 2013/0206141 A1    Aug. 15, 2013

Related U.S. Application Data

(62) Division of application No. 12/358,325, filed on Jan. 23, 2009, now Pat. No. 8,381,720.

(30) Foreign Application Priority Data

Jan. 24, 2008   (EP) ................................. 08001293

(51) Int. Cl.
*A61M 15/00*   (2006.01)

(52) U.S. Cl.
USPC ............. 128/203.15; 128/203.12; 128/203.21

(58) Field of Classification Search
USPC ............. 128/200.14, 200.21, 203.12, 203.15, 128/203.21, 200.17
See application file for complete search history.

(56) References Cited

U.S. PATENT DOCUMENTS

| 6,032,666 | A | 3/2000 | Davies et al. |
|---|---|---|---|
| 6,941,948 | B2 * | 9/2005 | Staniforth et al. ........ 128/203.21 |
| 2004/0035420 | A1 * | 2/2004 | Davies et al. ............ 128/203.15 |
| 2005/0081853 | A1 * | 4/2005 | Young et al. ............ 128/203.21 |
| 2007/0137645 | A1 | 6/2007 | Eason et al. |
| 2007/0267016 | A1 | 11/2007 | Thoemmes et al. |
| 2008/0196718 | A1 | 8/2008 | Connell et al. |
| 2008/0202515 | A1 | 8/2008 | Hodson et al. |
| 2009/0205656 | A1 | 8/2009 | Nishibayashi et al. |
| 2010/0139654 | A1 | 6/2010 | Thoemmes et al. |

FOREIGN PATENT DOCUMENTS

| GB | 2 407 042 A | 4/2005 |
|---|---|---|
| WO | 96/09085 A1 | 3/1996 |
| WO | 2004/093848 A2 | 11/2004 |
| WO | 2005/037353 A1 | 4/2005 |
| WO | 2006/071512 A1 | 7/2006 |
| WO | 2007/096111 A2 | 8/2007 |
| WO | 2007/118490 A1 | 10/2007 |

* cited by examiner

*Primary Examiner* — Jackie Ho
*Assistant Examiner* — Kathryn E Ditmer
(74) *Attorney, Agent, or Firm* — Roberts Mlotkowski Safran & Cole, P.C.; David S. Safran

(57) ABSTRACT

An inhaler for delivery of a powder-form inhalation formulation from a blister strip has a plurality of blister pockets and uses a pivotable mouthpiece cover to move the blister strip onward via a conveyor, wherein the mouthpiece cover is drivingly coupled with the conveyor by engaging an axle in a recess to drive a conveying wheel.

18 Claims, 17 Drawing Sheets

INHALER FOR DELIVERY OF A POWDER FORMULATION FROM A BLISTER STRIP

CROSS REFERENCE TO RELATED APPLICATION

This application is a division of U.S. patent application Ser. No. 12/358,325, filed on Jan. 23, 2009, now U.S. Pat. No. 8,381,720, which claims priority to European Patent Application No. EP08001293, filed Jan. 24, 2008, the contents of which are all hereby incorporated by reference in their entirety.

BACKGROUND OF THE INVENTION

1. Field of the Invention

The present invention relates to an inhaler for delivery of an inhalation formulation from a preferably band-shaped blister strip that has a plurality of blister pockets containing doses of the inhalation formulation.

2. Description of Related Art

UK Patent Application GB 2 407 042 A discloses an inhaler with a rolled-up blister strip. The inhaler comprises a manually operated, pivotable actuator which operates a conveyor for stepwise moving the blister strip. The actuator supports a piercer and an associated mouthpiece. By pivoting the actuator, the blister strip can be moved forward and blister pockets of the blister strip can be pierced one after the other. When a patient breathes in, an air stream passes through the previously pierced blister pocket, with the result that the inhalation formulation in the blister pocket mixes with the air and is discharged to the patient. Before use, a mouthpiece cover of the inhaler has to be opened. The mouthpiece cover can be pivoted around an axis that extends in a plane perpendicular to the pivot axis of the actuator.

SUMMARY OF THE INVENTION

A primary object of the present invention is to provide an inhaler of a simple and/or compact construction and/or with optimized design, handling and/or functionality.

The above object is achieved by an inhaler of the initially mentioned type in which the mouthpiece cover is coupled with the conveyor to drive the conveying wheel and to move the blister strip onward, and/or the axis of the actuator and/or conveying wheel extends coaxial to or is identical to the cover axis.

A pivotable mouthpiece cover is coupled with a conveyor to move a blister strip when the mouthpiece cover is operated. This allows a very simple construction and optimized handling.

According to another aspect of the present invention, which can be realized independently, the axis of the moveable mouthpiece cover extends coaxial with or is identical to the axis of the actuator and/or conveying wheel of the inhaler. This allows a very simple construction and optimized handling.

Further aspects, features, properties and advantages of the present invention are described in the subsequent description of a preferred embodiment, with reference to the accompanying drawings.

DETAILED DESCRIPTION OF THE INVENTION

In the figures, the same reference numbers are used for identical or similar parts, even if a repeated description is omitted. In particular, identical or corresponding advantages and properties then also result or may be achieved.

Figure 1:
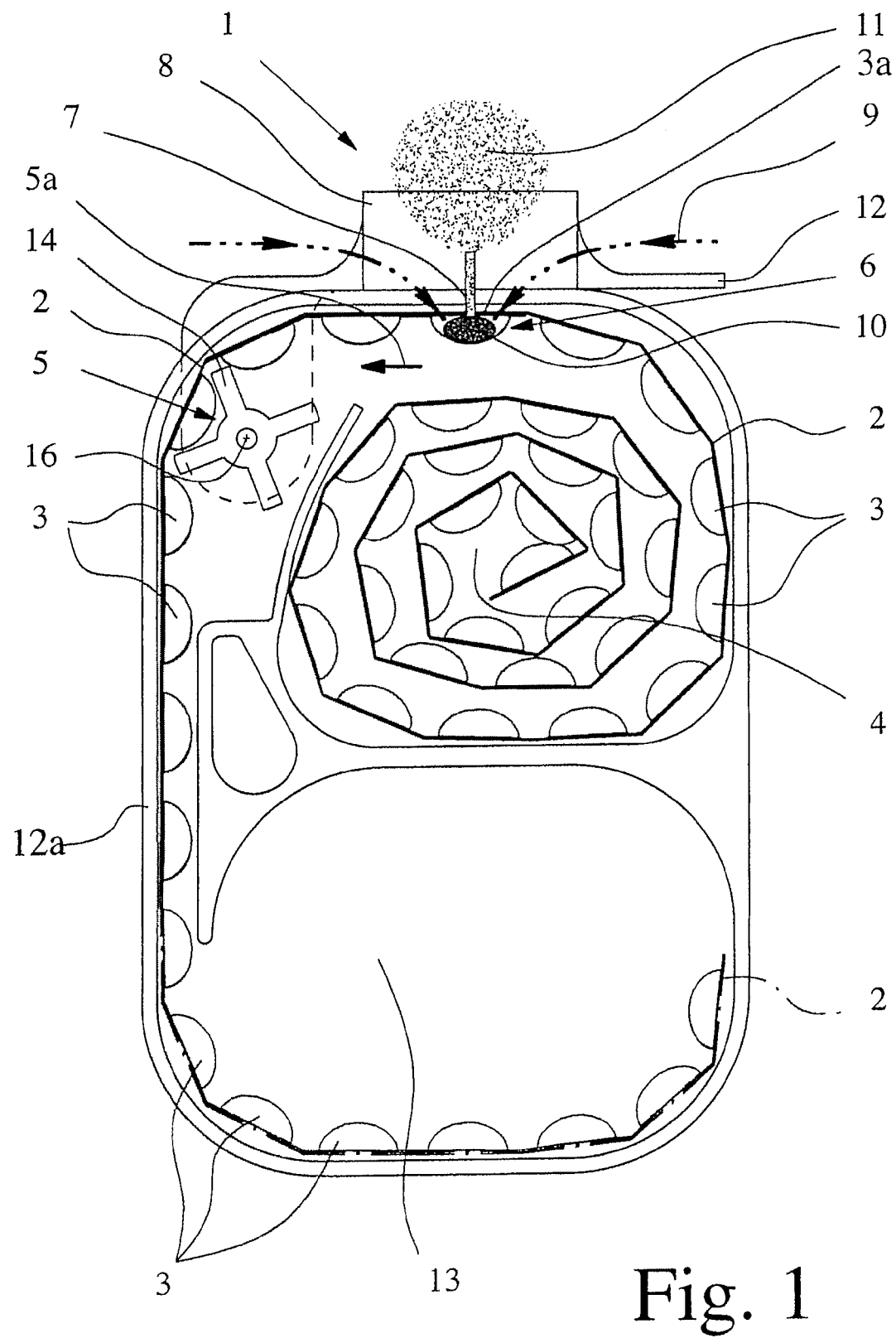
FIG. 1 is a schematic sectional view of an inhaler without the mouthpiece cover.

FIG. 1 shows a schematic sectional representation an inhaler 1. Preferably, the inhaler 1 is portable, works only mechanically and/or is hand-held.

The inhaler 1 serves to deliver a powdered inhalation formulation from a band-shaped blister strip 2. The blister strip 2 is finite, not forming an endless or closed loop. Blister strip 2 has a large number of blister pockets 3, each of which contains a respective dose of the loose inhalation formulation. Thus, the formulation is pre-metered.

The inhaler 1 has a reservoir 4 for the still unused blister strip 2 with closed (sealed) blister pockets 3. The blister strip 3 is rolled up or wound up in the reservoir 4. In the representative example shown, the reservoir 4 is formed such that the blister strip 2 can be moved outwards or pulled out of the reservoir 4 as easily as possible.

In the present embodiment, the blister strip 2 is directly received in the reservoir 4. However, instead of this, a cassette, a container, a drum or the like can also be fitted or inserted with the blister strip 2 into the inhaler 1 or the reservoir 4.

The inhaler 1 has a conveyor 5 for stepwise onward movement of the blister strip 2, in the direction of arrow 5a, by one blister pocket 3 in each case, in order to feed the blister pockets 3 successively to an opening and/or removal position 6 where the respective blister pocket 3 is opened and can be emptied.

The blister pockets 3 can be opened respectively preferably by means of a piercing member 7 which punctures or cuts open a lid 3a of the respectively aligned blister pocket 3 in position 6. The piercing member 7 fluidically connects the blister pocket 3 with an adjacent mouthpiece 8 of the inhaler 1.

During or for inhalation, a patient or user places the mouthpiece 8 in his/her mouth and breathes in. The respectively opened blister pocket 3, into which the piercing member 7 extends, is thereby emptied by sucking in. An air stream 9 of ambient air is sucked in and passed through the opened blister pocket 3 such that the loose powder 10 (forming the inhalation formulation) is dispensed only from the actually opened blister pocket 3 with the sucked-in ambient air as an aerosol cloud 11 via the mouthpiece 8. This situation is schematically represented in FIG. 1.

The inhaler 1 has a preferably manually actuatable, lever-like actuator 12 that is pivotally mounted to a housing 12a of the inhaler 1. The piercing member 7 and the mouthpiece 8 are attached to and supported by the actuator 12.

The actuator 12 is pivotally supported by the housing 12a, namely directly by at least one respective sliding bearing or indirectly by other components as appropriate.

The actuator 12 is operable (pivotable) to cause the piercing member 7 to puncture the lid 3a of the respectively aligned blister pocket 3 in position 6 below the mouthpiece 8.

Figure 3:
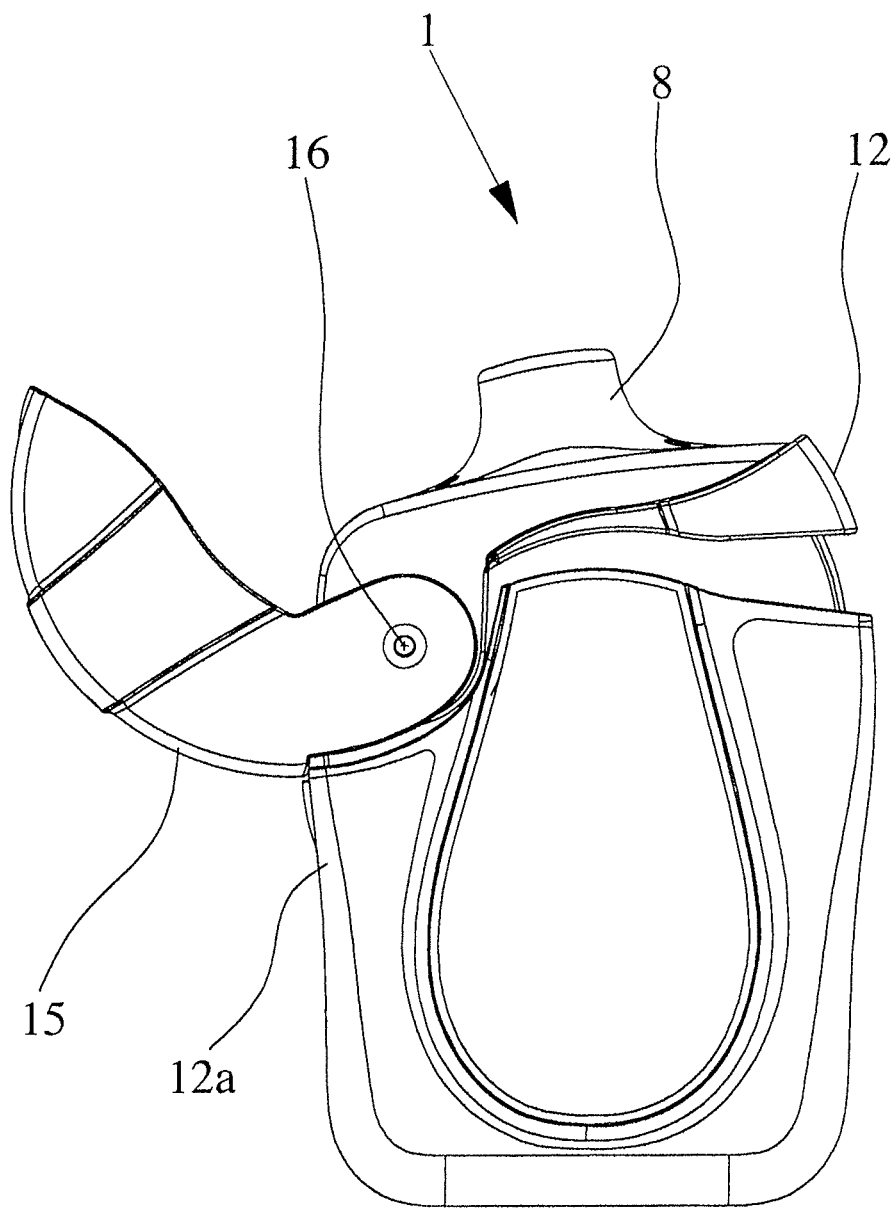
FIG. 3 is a schematic view of the inhaler with the mouthpiece cover opened.

When the actuator 12 swivels from the position shown in FIG. 1 (here, counterclockwise) to its (partially) opened position shown in FIG. 3, the piercing member 7 is withdrawn from the last-pierced blister pocket 3.

Then, the blister strip 2 is moved forward by one blister pocket 3, so that the next blister pocket 3 is moved in position 6. This will be explained in more detail later.

When the actuator 12 is swung back into the position shown in FIG. 1, i.e., is manually moved back, the next aligned blister pocket 3 of the blister strip 2 is punctured by the piercing member 7 and thereby opened. Then, the inhaler 1 is activated and the next inhalation can take place.

The inhaler 1 has a receiving space or apparatus 13 to receive or store the used part of the blister strip 2. The receiving space or apparatus 13 is formed such that the used part can be wound up. FIG. 1 shows a situation with essentially filled reservoir 4 and still essentially empty receiving space 13.

The conveyor 5 comprises a conveying wheel 14, which can engage between the blister pockets 3 and thus convey the blister strip 2 in form-locking or form-fit manner. This allows very secure or precise moving or indexing of the blister strip 2 as desired and/or necessary.

The conveyor 5 or its conveying wheel 14 is arranged between the reservoir 4 and the receiving apparatus 13, in particular between the removal position 6 and the receiving apparatus 13, thus, after the emptying of the blister pockets 3.

The pivot axis of the actuator 12 is coaxial with the rotation axis of the conveying wheel 14. In particular, the actuator 12 may be supported by an axle of the conveying wheel 14 and/or by the housing 12a.

Figure 2:
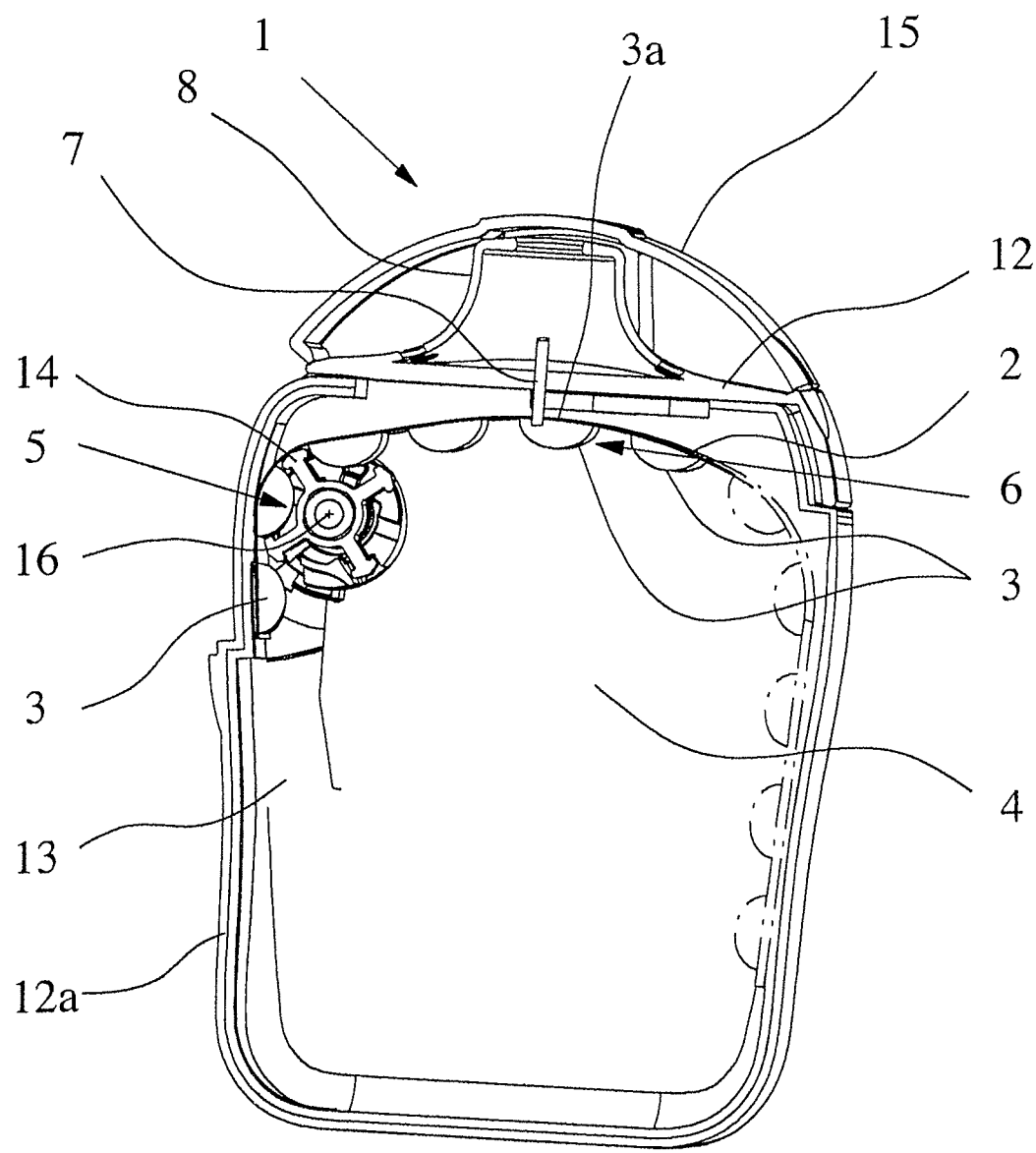
FIG. 2 is a schematic sectional representation of the inhaler with a closed mouthpiece cover.

The inhaler 1 comprises a mouthpiece cover 15. The mouthpiece cover 15 is not shown in FIG. 1 which explains only the basic principle of the inhaler 1, but is shown in FIG. 2 which shows a more realistic, but still schematic sectional view of the inhaler 1. FIG. 2 shows the inhaler 1 with mouthpiece cover 15 closed, wherein the blister strip 2 has been partly omitted for illustration purposes. FIG. 3 shows the inhaler 1 with mouthpiece cover 15 completely opened.

The mouthpiece cover 15 is pivotable around a cover axis 16 which is indicated in FIGS. 2 & 3 and extends perpendicular to the plane of these drawing figures.

Preferably, the mouthpiece cover 15 axially covers an axle or the axis of the actuator 12 and/or conveying wheel 14.

The pivot axis of the actuator 12 extends coaxial to or with the cover axis 16. The rotation axis of the conveying wheel 14 extends coaxial to the cover axis 16 and to the pivot axis of the actuator 12.

The conveyor 5, or its conveying wheel 14, is driven by the mouthpiece cover 15, namely by the pivotal movement of the mouthpiece cover 15. In particular, the blister strip 2 is moved forward, when the mouthpiece cover 15 is opened. Preferably, only part of the opening movement of the mouthpiece cover 15 actuates or operates the conveyor 5 or its conveying wheel 14 to move the blister strip 2 forward. In particular, the mouthpiece cover 15 is coupled with the conveyor 5 such that indexing occurs only during a portion of the movement of the mouthpiece cover 15 in one direction, here in the opening direction.

When the mouthpiece cover 15 is opened, starting from the completely closed position shown in FIG. 2, in a first phase of the opening movement, for example, up to a first angle of about 10, 20, 30 or 40 degrees, in particular, about 35 degrees, the blister strip 2 is not moved due to a respective free-wheel or lost motion coupling (explained later) between the mouthpiece cover 15 and the conveying wheel 14.

First of all, the actuator 12 has to be moved or opened in order to withdraw the piercing member 7 from the previously pierced and usually/already emptied blister pocket 3. This opening movement of the actuator 12 can be performed manually. However, the actuator 12 preferably opens automatically or together with the mouthpiece cover 15 when opening the mouthpiece cover 15.

In particular, the mouthpiece cover 15 is opened up to the first angle. When the mouthpiece cover 15 reaches this angle or reaches or exceeds the opened position of the actuator 12, the actuator 12 can flip automatically open into its opened position shown in FIG. 3, in particular, due to a biasing or spring means (not shown) or the like. However, it also possible and preferred in the present embodiment that the actuator 12 moves jointly with the mouthpiece cover 15 in the first phase of the opening movement (e.g., due to a ratchet mechanism, a spring, a driving or coupling means which is explained later, or the like) until the actuator 12 reaches its opened position (preferably at on opening angle of about 5 to 15 degrees, here about 10 degrees) or the first angle.

The opened position of the actuator 12 is preferably set such that the piercing member 7 is not exposed to the exterior and/or that the inhaler 1 is not completely opened in order to avoid or at least minimize any potential external influences and/or to optimize the handling.

In order to limit the open position of the actuator 12 (first phase), the opening or pivot range of the actuator 12 is smaller than that of the mouthpiece cover 15, in particular, and/or is restricted to the opening angle, preferably at most 20 degrees, in particular, to about 10 degrees or less.

However, it is also possible that the actuator 12 is not limited in its opening position, but can open or pivot as far as the mouthpiece cover 15, in particular, jointly with the mouthpiece cover 15.

During the further opening (second phase) of the mouthpiece cover 15, the conveyor 5 or its conveying wheel 14 is actuated to move or index the blister strip 2 by one blister pocket 3 onward to the next blister pocket 3 that is to be emptied. In particular, the mouthpiece cover 15 is pivoted during the second phase together with indexing of the actuator 12. The blister movement happens preferably up to the complete opening of the mouthpiece cover 15 shown in FIG. 3.

Preferably, only when the mouthpiece cover 15 is opened completely, i.e., reaches its end position and the actuator 12 is then closed, the movement of the blister strip 2 is set or fixed by a respective mechanism (explained later) and/or decoupled from the mouthpiece cover movement to keep the next blister pocket 3 in position 6 for puncturing. However, if the mouthpiece cover 15 is not fully opened and closed again or if the actuator 12 has not been closed after the mouthpiece cover 15 has been fully opened, then, the blister strip 2 may be moved backward during closure of the mouthpiece cover 15. This facilitates operation of the inhaler 1, and in particular, prevents incomplete or unintended operation of the mouthpiece cover 15 from resulting in an undesired incomplete or unintended, movement or positioning of the blister strip 2 and eventually in an undesired opening of the next blister pocket 3.

Preferably, a lock (explained later) is provided so that the opened actuator 12 can be closed again only if the mouthpiece cover 15 has been fully opened and the actuator 12 has been closed. Thus, the piercing member 7 cannot be pushed against an area of the blister strip 2 without or beside a blister pocket 3.

When the mouthpiece cover 15 has been fully opened and the next blister pocket 3 has been moved into position 6, the actuator 12 can be pivoted back, i.e., reset, in order to pierce the already aligned, still closed blister pocket 3. Then, the inhaler 1 is ready for inhalation, i.e., activated as already described.

After inhalation, the inhaler 1 can be closed by pivoting back the mouthpiece cover 15 into its closed position.

In order to operate the conveyor 5 or its conveying wheel 14 by movement of the mouthpiece cover 15 as described above or in any other suitable manner, the mouthpiece cover 15 is coupled with the conveyor 5, in particular, the conveying wheel 14, via the already mentioned free-wheel and/or via a suitable transmission, a slipping clutch or any other suitable coupling or the like.

Preferably, the free-wheel, transmission, lost motion coupling or the like is integrated into or located adjacent to the conveying wheel 14 or a respective axle.

Further details of the preferred embodiment of the inhaler 1 will be explained in the following with reference to the further figures.

Figure 4:
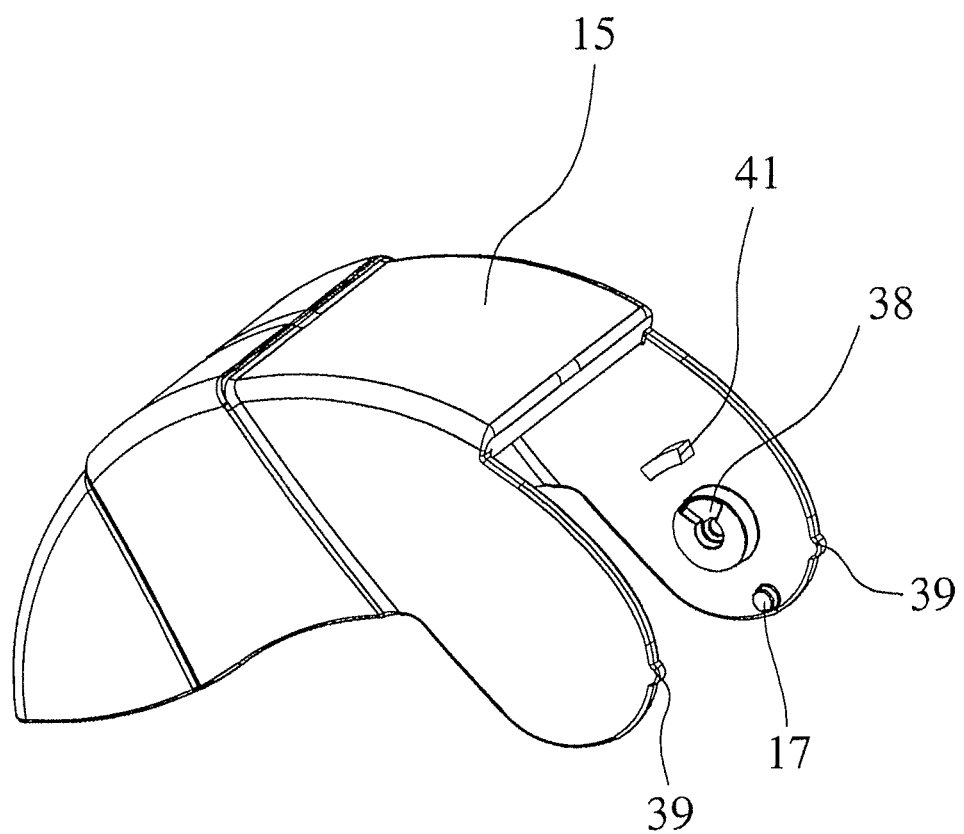
FIG. 4 is a perspective side view of the mouthpiece cover.
Figure 5:
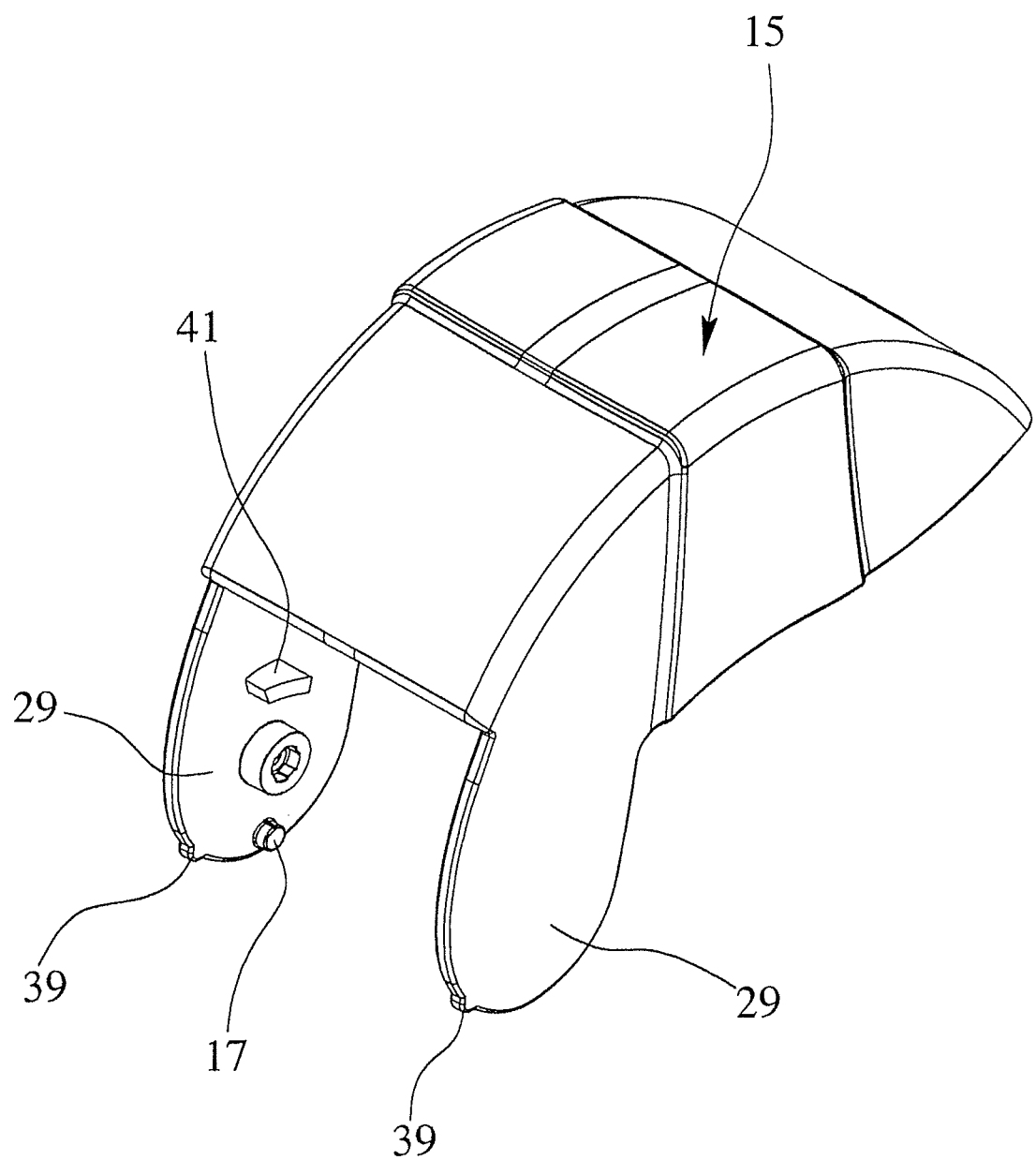
FIG. 5 is another perspective side view of the mouthpiece cover.

The driving or coupling means for moving the actuator 12 from its closed position shown in FIG. 1 to its opened position shown in FIG. 3 preferably comprises at least one cam or protrusion 17 cooperating with an associated recess 18. Preferably, two protrusions 17 are provided at opposite sides at the mouthpiece cover 15 and/or adjacent to the cover axis 16 as schematically shown in FIGS. 4 & 5 representing different side views of the mouthpiece cover 15. In particular, the protrusions 17 are pin-shaped or cylindrical.

Figure 6:
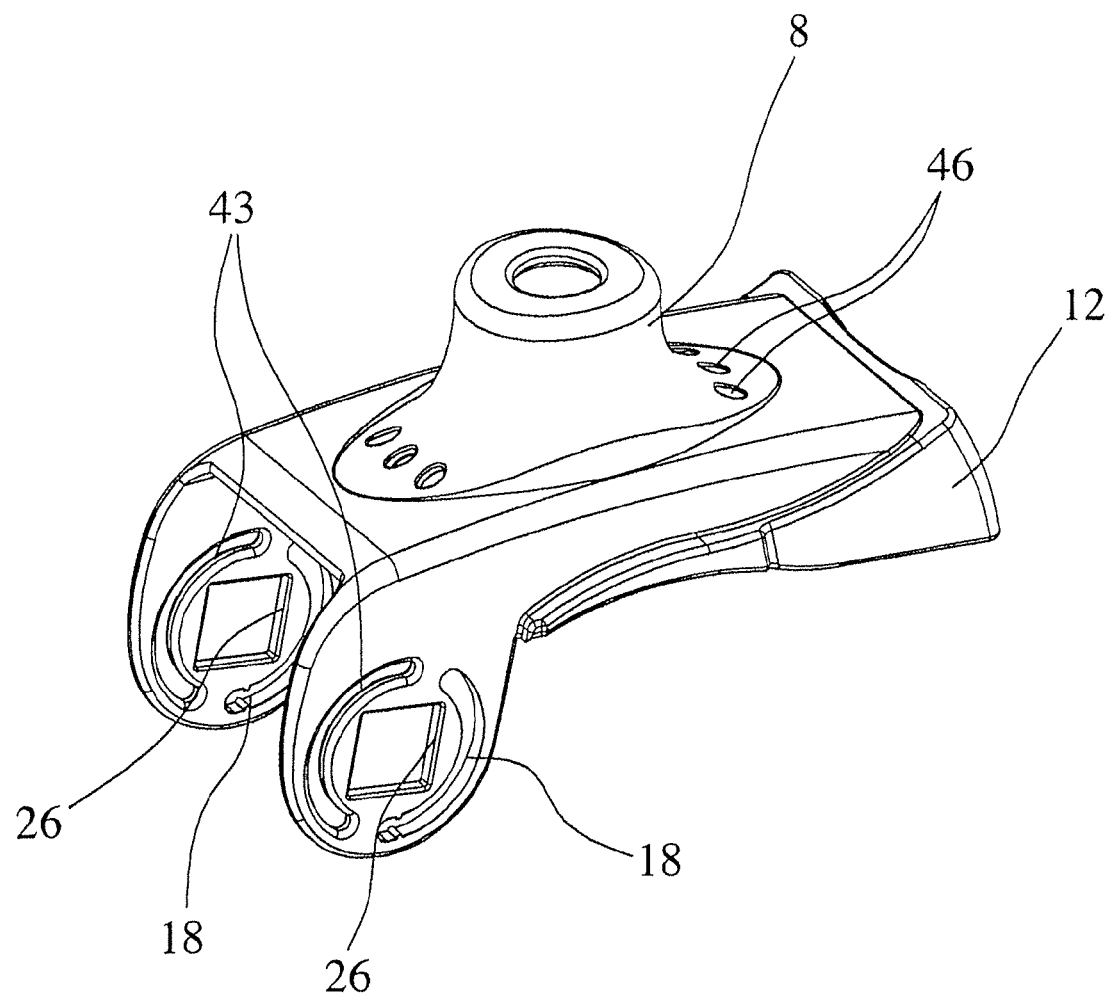
FIG. 6 is a perspective side view of an actuator of the inhaler.

Preferably, two recesses 18 are provided at or formed by the actuator 12 (as schematically shown in the perspective side view of the actuator 12 in FIG. 6) which cooperate with the associated protrusions 17.

Figure 20:
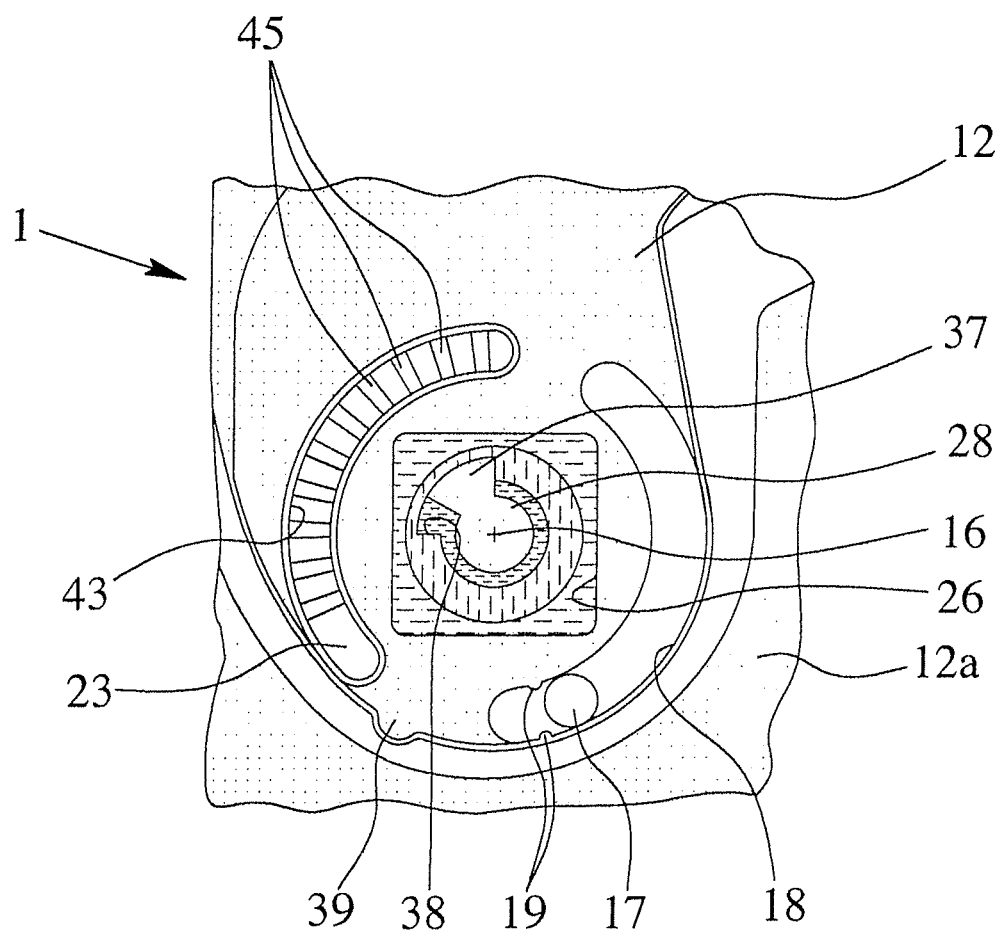
FIG. 20 is a schematic view of a free-wheel of the inhaler.

Each protrusion 17 extends or engages into its associated recess 18 and can move along the recess 18 corresponding to the pivotal movement or position of the mouthpiece cover 17 relative to the actuator 12 (see also FIG. 20). Therefore, each recess 18 extends circumferentially around the cover axis 16 and/or may form a pivotal restriction or stop for the mouthpiece cover 15.

Figure 7:
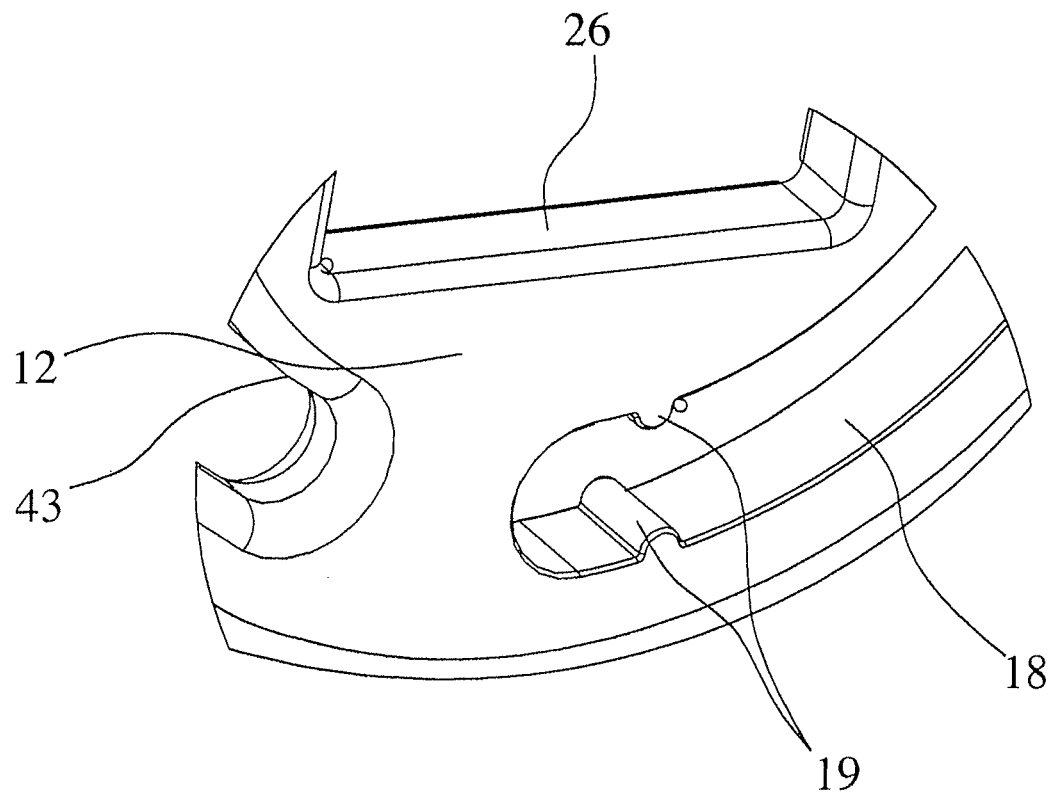
FIG. 7 is a partial enlargement of FIG. 6.

Each recess 18 preferably comprises a holding or clamping means, here one or two noses 19 as shown in FIG. 7 representing a partial engagement of FIG. 6. This holding or clamping means holds the associated protrusion 17 at a position within the recess 18 (here at one end of the recess 18) so that the actuator 12 is pivoted together with the mouthpiece cover 15 when the mouthpiece cover 15 is opened in the first phase. Only when the actuator 12 is held manually in its closed position or reaches its opened position, can the protrusion 17 override the holding or clamping means, here the noses 19, and freely move along the further recess 18 so that the actuator 12 is decoupled from the further pivotal movement of the mouthpiece cover 15.

In order to clean the mouthpiece 8, for example, it is possible to manually hold the actuator 12 down when opening the mouthpiece cover 15. In this case, the protrusions 17 directly override the cam means (noses 19). Thus, it is possible to open the mouthpiece cover 15—at least up to the first angle—without movement of the actuator 12 and/or without onward movement of the blister strip 2.

Figure 8:
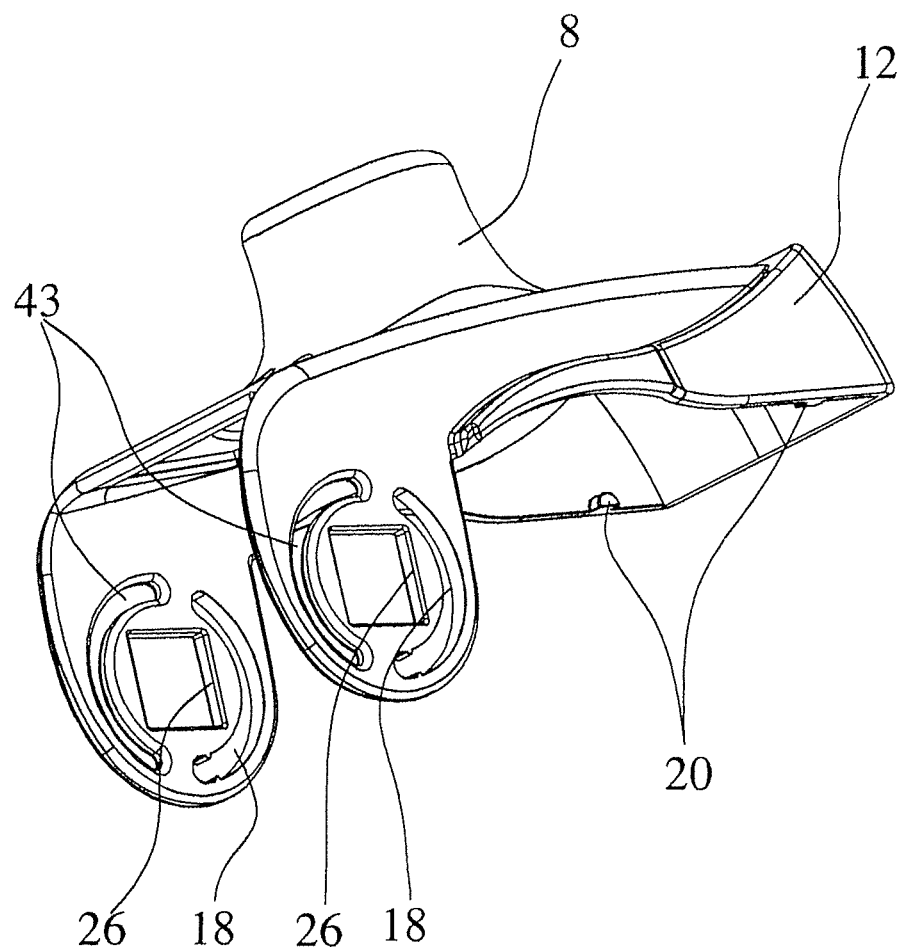
FIG. 8 is another perspective view of the actuator.

The inhaler 1 preferably comprises a restriction means for restricting the opening movement of the actuator 12. In particular, the restricting means defines the opened position of the actuator 12. In the present embodiment, the restricting means is formed by one or two stops 20 formed e.g., at the inner side of actuator 12 (one stop 20 is shown in the perspective view according to FIG. 8). In particular, the stops 20 protrude from opposite sides towards the housing 12a of the inhaler 1.

Figure 9:
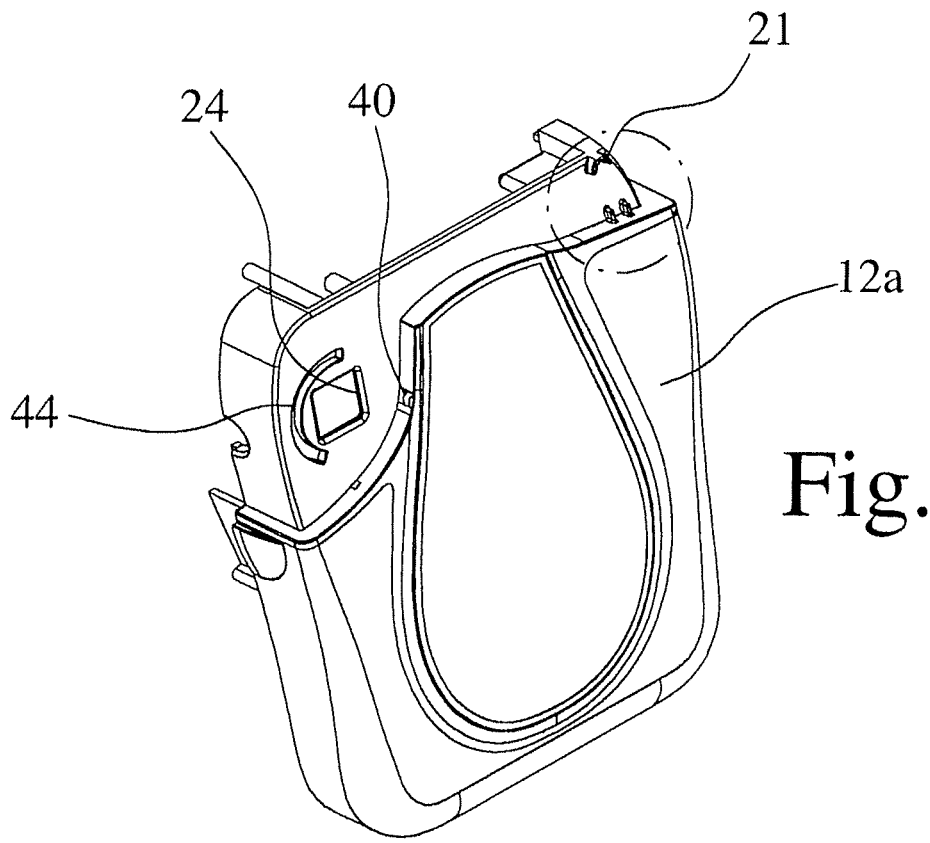
FIG. 9 is a perspective view of one half of a housing of the inhaler.
Figure 10:
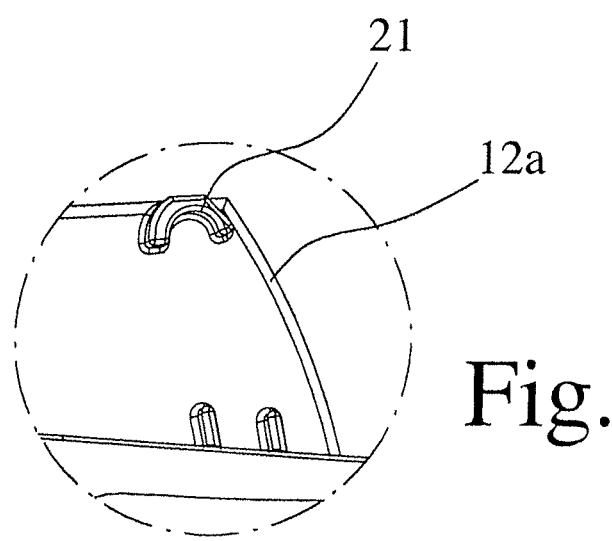
FIG. 10 is an enlargement of the encircled detail in FIG. 9.
Figure 11:
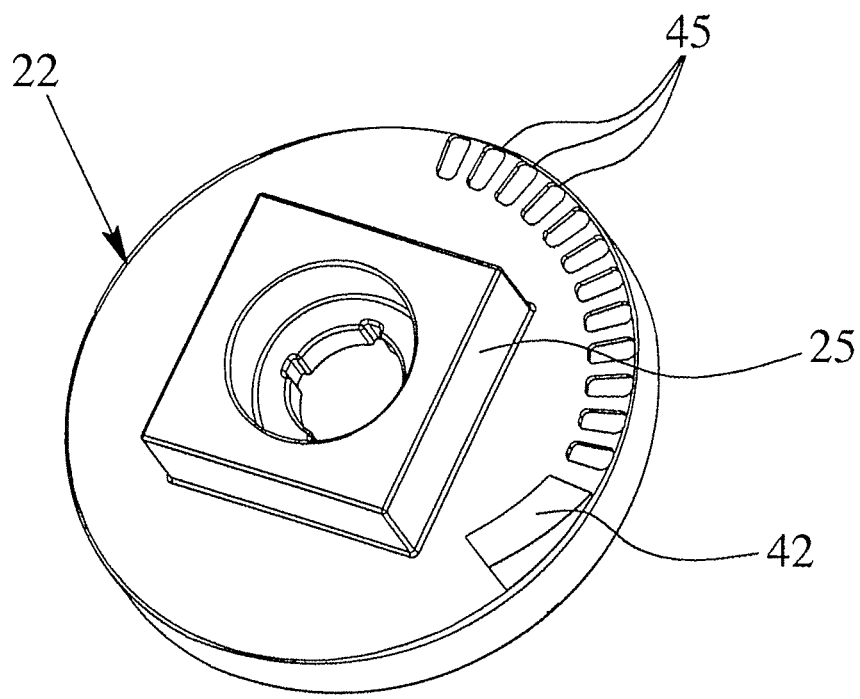
FIG. 11 is a perspective view of a first lock element of the inhaler.

The housing 12a comprises associated counterstops 21 (one counterstop 21 is shown in the perspective view of one half of the housing 12a of FIG. 9 and in the partial enlargement of FIG. 10) so that the stop 20 abuts at its associated counterstop 21 when the actuator 12 reaches its opened position. Thus, the opened position is defined and any further opening of the actuator 12 is prevented by the abutment.

In the preferred embodiment, the counter stops 21 preferably extend in opposite directions and/or on opposite sides of the housing 12a.

However, other constructional solutions are possible to realize the driving or coupling means and/or the restriction means described above. For example, the driving or coupling means can comprise or be formed by a spring (not shown) biasing the actuator 12 into its opened position and by a respective actuator lock to hold the actuator 12 in the closed position as desired.

When the actuator 12 reaches its opened position it is locked. The actuator lock preferably comprises at least one lock element, preferably two lock elements 22, 23 as shown in FIGS. 11 to 14, for locking the actuator 12 with the housing 12a or any other suitable component of the inhaler 1.

In particular, the lock works as follows. This explanation focuses on one lock element 22. If the additional lock element 23 is provided, the explanation preferably applies in a similar manner.

The lock element 22, in the locked position, blocks any pivoting of the actuator 12 relative to the housing 12a. The lock element 22 comprises a canted or polygonal protrusion or portion 25 (preferably square in cross section) cooperating with and extending through a corresponding (complementary) canted or polygonal opening 24 in the housing 12a (see, FIG. 9) so that the lock element 22 cannot rotate around the axis of the actuator 12. However, the lock element 22 is axially moveable with regard to the axis of the actuator 12. It is biased outwards or towards a flap 29 of the actuator 12 so that the portion 25 can axially move into a respective opening 26 of the actuator 12 (see, FIGS. 6 & 8) when the actuator 12 reaches its opened position. The opening 26 is also canted or polygonal as the opening 24 and/or in a complementary manner to the portion 25. Thus, the actuator 12 can be blocked against rotation relative to the housing 12a by the portion 25 engaging into the opening 26. This blocked state will be referred to herein as "actuator locking."

The actuator locking prevents closing of the actuator 12 during movement of the blister strip 2. Thus, piercing can be prevented during movement or any undefined positioning of the blister strip 2.

The inhaler 1 comprises a spring 27 in order to bias the at least one lock element 22, preferably both lock elements 22, 23, axially into engagement with the actuator 12 for actuator locking.

Figure 15:
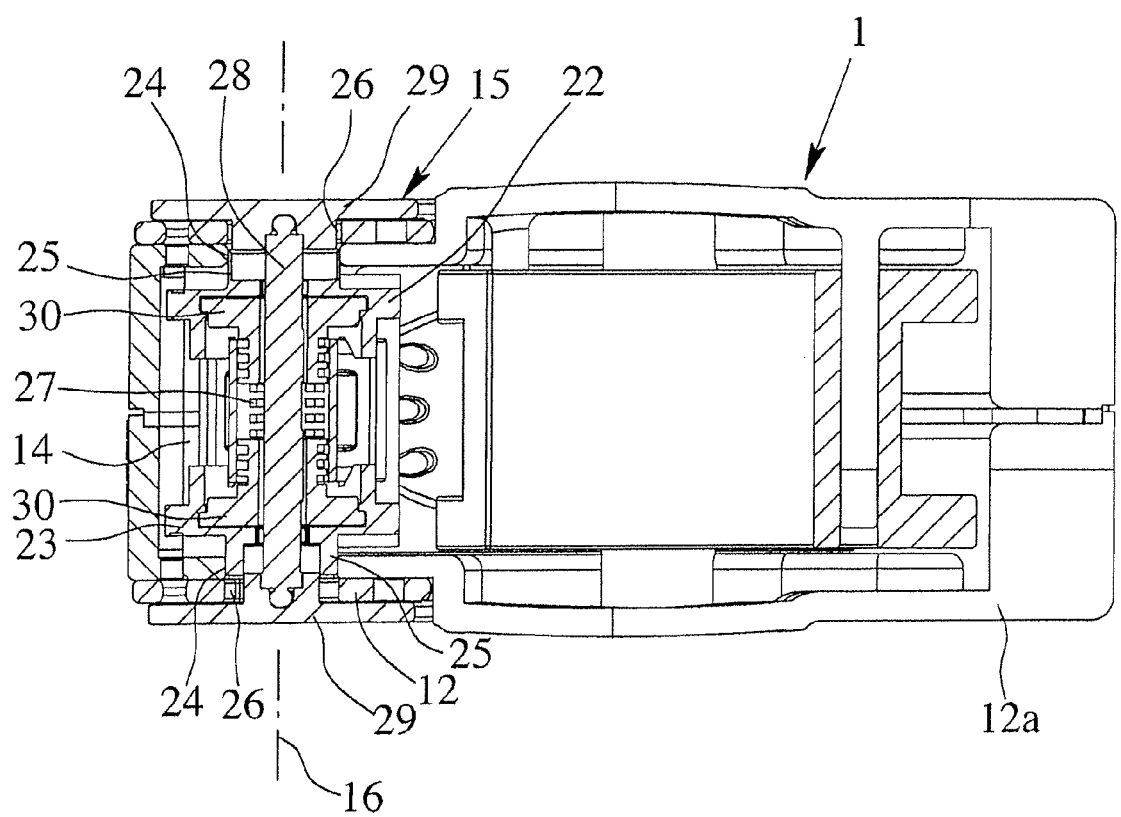
FIG. 15 is a horizontal sectional view of the inhaler.
Figure 16:
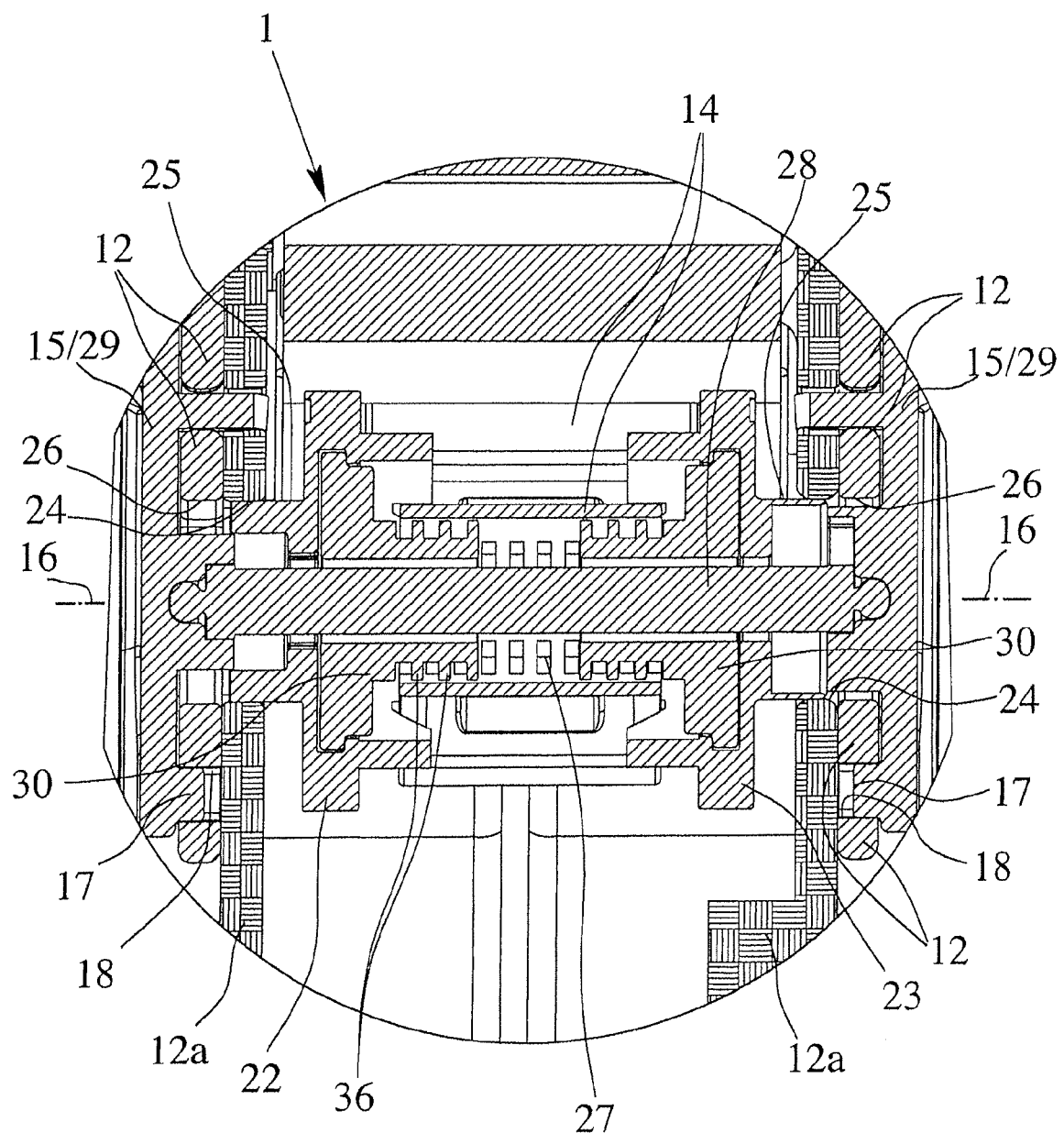
FIG. 16 is a partial vertical sectional view of the inhaler.

FIG. 15 is a horizontal section of the inhaler 1 in the plane of the axis of the actuator 12, i.e., also in the plane of the cover axis 16 in the state when the mouthpiece cover 15 is closed, and in which the spring 27 is shown. FIG. 16 shows a partial, enlarged, vertical, sectional view of the inhaler 1 in the plane of the axis of the actuator 12 and the cover axis 16, i.e., perpendicular to the section according to FIG. 15, but also in the state with closed mouthpiece cover 15.

The spring 27 is arranged between the lock elements 22, 23 and axially biases the lock elements 22, 23 in opposite directions. The canted portions 25 of lock elements 22, 23 are guided within the associated openings 24 in the housing 12a, but do not engage into the openings 26 of the actuator 12 in the state shown.

An axle 28 extends through the lock elements 22, 23 and through the preferably helical spring 27 and forms the cover axis 16. The axle 28 can rotate in or relative to the lock elements 22, 23 which cannot rotate due to their outer form engaging with a stationary part of the inhaler 1, such as the housing 12a. It is noted that the lock elements 22, 23 are essentially mirror-symmetrical and/or have different through holes or openings for axially inserting the axle 28.

The axle 28 extends into axial flaps 29 of the mouthpiece cover 15 which axially cover the conveyor 5, the housing 12a, the lock elements 22, 23, the axle 28 and/or the conveying wheel 14. In particular, the conveying wheel 14 is hollow. The axle 28 is extending through the conveying wheel 14. The spring 27 is arranged within the conveying wheel 14 and/or encompassing the axle 28.

The axle 28 is preferably driven or rotated by the mouthpiece cover 15. Preferably, the axle 28 forms a pivotal bearing for the mouthpiece cover 15 or vice versa. In particular, the axle 28 forms the cover axis 16.

Figure 17:
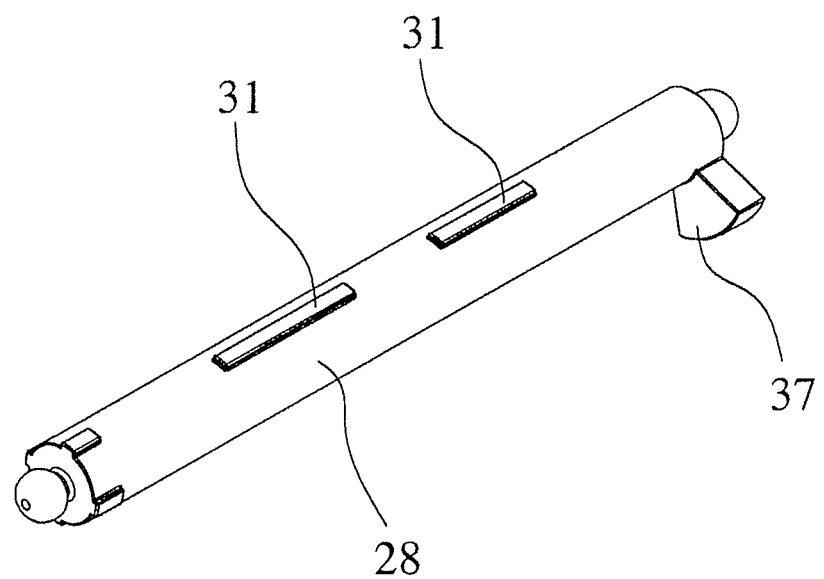
FIG. 17 is a perspective view of an axle of the inhaler.

A coupling element 30 is arranged between the spring 27 and each lock element 22, 23, respectively. The coupling elements 30 are axially moveable together with the lock elements 22, 23 on the axle 28. However, the coupling elements 30 cannot rotate relative to the axle 28. The coupling elements 30 are rotationally rigidly connected with the axle 28, in particular, via radially engaging keys 31, ridges or the like as schematically shown in FIG. 17.

Figure 18:
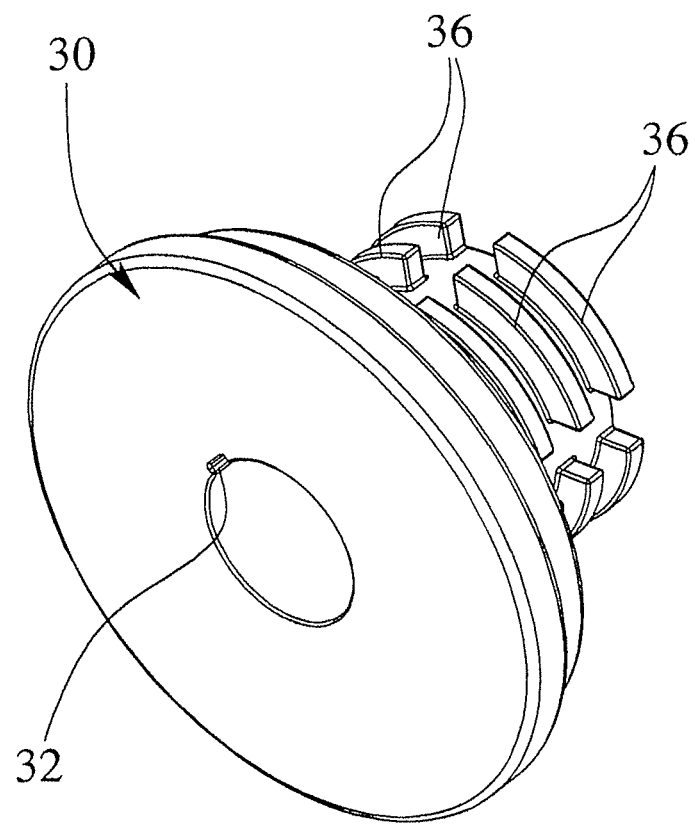
FIG. 18 is a perspective view of a coupling element.

In particular, each coupling element 30 comprises an inner axial groove 32 (see, FIG. 18) into which the associated key 31, ridge or the like can radially engage in order to rotationally couple the coupling element 30 to the axle 28.

Figure 12:
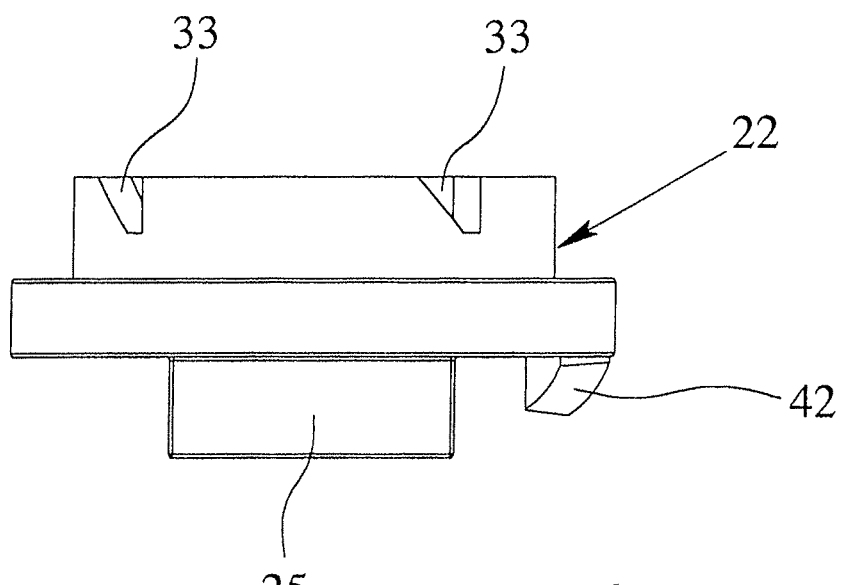
FIG. 12 is a side view of the first lock element.
Figure 13:
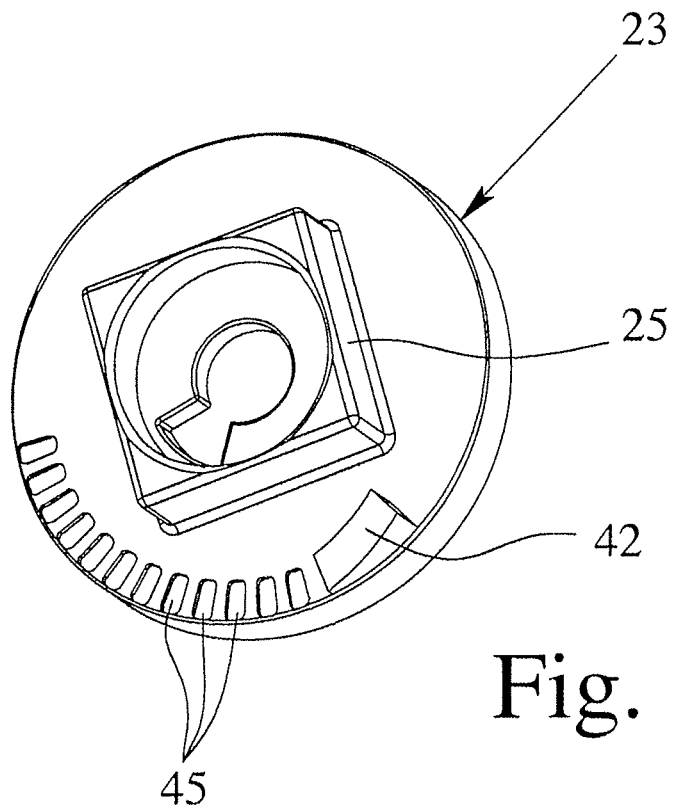
FIG. 13 is a perspective view of a second lock element of the inhaler.
Figure 14:
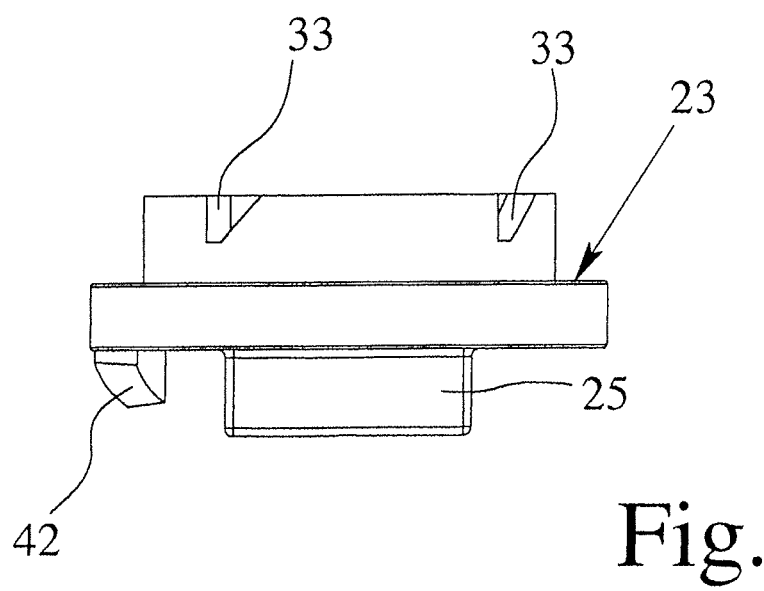
FIG. 14 is a side view of the second lock element.
Figure 19:
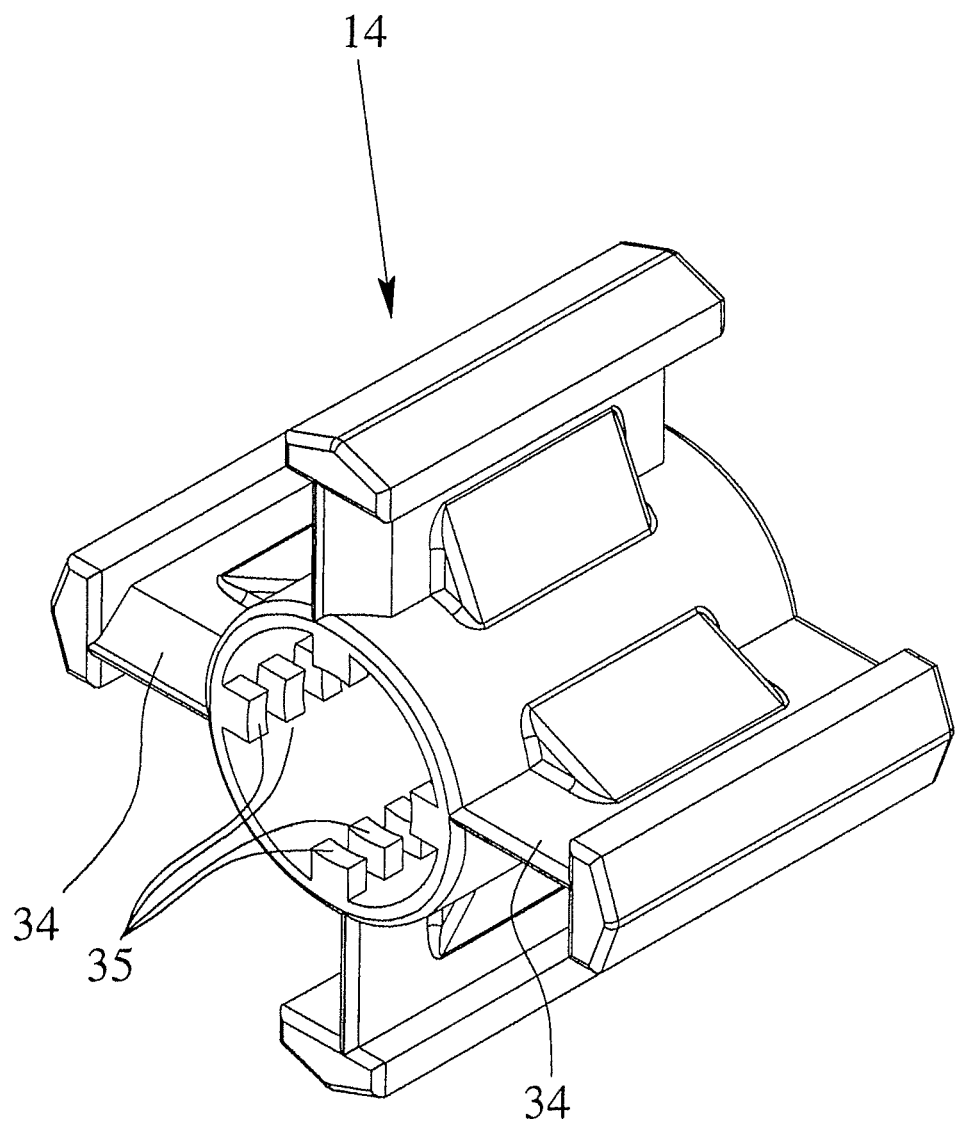
FIG. 19 is a perspective view of a conveying wheel of the inhaler.

With closed mouthpiece cover 15 and/or with the coupling elements in the axially inner position, the conveying wheel 14 (shown in FIG. 19) is rotationally decoupled from the coupling element 30. Instead, the lock elements 22, 23 axially engage the conveying wheel 14 in this state. In particular, axially open notches 33, formed in an annular portion of the lock element 22, 23, respectively, as shown in FIGS. 12 & 14, engage with the conveying wheel 14, in particular, with radially extending ridges 34 shown in FIG. 19.

When the actuator 12 reaches its opened position and the actuator locking is reached, the following happens. The lock elements 22, 23 and the coupling elements 30 move axially outwards due to spring 27. Thus, the rotational (axial) locking between the lock elements 22, 23 and the conveying wheel 14 is unlocked.

Simultaneously, the axially shifted coupling elements 30 couple the conveying wheel 14 rotationally to the axle 28. This rotational coupling is achieved in the present embodiment by the cooperation of inner teeth 35 of the conveying wheel 14 (see, FIG. 19) with outer teeth 36 of the coupling element 20 (see, FIG. 18). In particular, the teeth 35/36 are arranged in different rows that are circumferentially distributed and extend in an axial direction. Each rows has multiple spaced teeth 35/36. Thus, the teeth 35, 36 can rotationally couple and decouple the respective coupling element 30 with the conveying wheel 14 depending on the axial position of the coupling element 30 relative to the conveying wheel 14. However, other constructional solutions are possible as well.

In the actuator locking state, the conveying wheel 14 is rotational rigidly coupled to the axle 28 as described above, i.e., rotation of the axle 28 drives the conveying wheel 14, and thus, moves the blister strip 2 onwards.

As already mentioned, the mouthpiece cover 15 can be opened further, up to the first angle, without onward movement of the blister strip 2. This is preferred in order to allow a wide opening of the mouthpiece cover 15 so that the mouthpiece cover 15 does not disturb during inhalation. In the present embodiment, namely, a rotational movement of the mouthpiece cover 15 of about 90° is sufficient to move the blister strip 2 by one blister pocket 3 to the next blister pocket 3. In order to achieve a fully opened position of the mouthpiece cover 15 that does not disturb a user or patient (not shown) of the inhaler 1, the first angle is preferably more than 20 degrees, in particular more than 30 degrees, preferably about 35 degrees, i.e., much greater than the angle of the actuator 12 in its opened position. This results in an angle much greater than 90° of the mouthpiece cover 15 in the completely opened position.

As already mentioned, a free-wheel, lost motion, connection is preferably provided in order decouple the axle 28 when the mouthpiece cover 15 is opened up to the first angle. The free-wheel is preferably formed by a radial wing 37 of the axle 28 (see, FIG. 17) cooperating with a respective engagement portion 38 formed at the mouthpiece cover 15 (see, FIG. 4). The schematic section of the inhaler 1 in the region of the partially opened mouthpiece cover 15 of FIG. 20 explains the cooperation of the wing 37 with the engagement portion 38. In particular, the engagement portion 38 forms a key-hole-like recess or recessed segment so that the wing 37 of axle 28 can freely rotate around cover axis 16 within a limited angular range which permits movement of the mouthpiece cover 15 from the completely closed position to the first angle without rotation of the axle 28.

FIG. 20 shows the situation where the mouthpiece cover 15 has reached the first angle. The engagement portion 38 or a side wall thereof has just abutted at one side of the wing 37. During further opening of the mouthpiece cover 15 (rotation in counterclockwise direction in the representation according to FIG. 20), the wing 37, and thus, the axle 28 will be rotated together with the mouthpiece cover 15 (second phase of opening) until the fully opened position is reached. This rotation of the axle 28 during the second phase drives the conveying wheel 14 via the coupled coupling elements 30, and consequently, moves the blister strip 2 forward by one blister pocket 3.

Other designs of the free-wheel are possible as well. Alternatively or additionally, the free-wheel can be integrated or arranged at any other position or between other components in the drive train between the mouthpiece cover 15 and the conveying wheel 14. Further, the free-wheel could be integrated into the coupling, provided by the coupling elements 30 and the conveying wheel 14, or any other coupling or vice versa.

FIG. 20 also shows the protrusion 17 of mouthpiece cover 15 which has already left its initial position at the left-hand side of recess 18 because the mouthpiece cover 15 has already been opened beyond the opened position of the actuator 12, namely up to the first angle.

When the mouthpiece cover 15 reaches its fully opened position, the mouthpiece cover 15 is preferably held in the fully opened position by at least one cam 39 formed on the mouthpiece cover 15 (see, FIG. 4) engaging at least one notch 40 formed on the housing 12a (see, FIG. 9). Thus, a holding effect is achieved. However, the holding effect is such that the engagement of the cams 39 with the notchs 40 can be released or overcome by manually closing the mouthpiece cover 15.

When the mouthpiece cover 15 has been fully opened, the actuator locking is preferably released. In particular, the lock elements 22, 23 are moved radially inwards just when the mouthpiece cover 15 reaches its fully opened position so that the actuator 12 can be manually closed to pierce the next blister pocket 3 which has been aligned by the onward movement of the blister strip 2 due to the opening of the mouthpiece cover 15. The axial inward movement of the lock elements 22, 23 results also in a central alignment of the conveying wheel 14, and thus, of the blister pocket 3 that is to be opened. Also, this results in rotational locking of the conveying wheel 14 by axial engagement of the lock elements 22, 23. In addition, the axial inward movement of the coupling elements 30 caused by the axial inward movement of the lock elements 22, 23 results in decoupling of the conveying wheel 14 form the axle 28.

The mouthpiece cover 15 preferably comprises means, such as at least one or more ramps 41 as shown in FIGS. 4 & 5 which cooperate with associated means, such as at least one or more ramps 42 on the lock elements 22, 23 (see, FIGS. 11 to 14). The ramps 41, 42 project axially and are inclined in a circumferential direction. The ramps 41, 42 can interact through respective openings 43 in the actuator 12 (see, FIGS. 6 & 8) and openings 44 in the housing 12a (see, FIG. 9) and are arranged and dimensioned such that the lock elements 22, 23 are inwardly pushed just when the mouthpiece cover 15 reaches its fully opened position to unlock the actuator 12, to engage the conveying wheel 14 and to decouple the coupling elements 30 from the conveying wheel 14.

Then, the actuator 12 can be manually closed. This results in a rotation of the openings 26 in the actuator 12 so that the lock elements 22 and 23 cannot be axially moved outwards again even if the mouthpiece cover 15 closed again releasing the engagement of the ramps 41, 42.

Preferably, the inhaler 1 has a lock against incomplete opening of the mouthpiece cover 15 and/or against closure of the mouthpiece cover 15 before the actuator 12 has been manually closed. This lock is preferably formed by a ratchet mechanism. The ratchet mechanism can be formed on only one side or on both sides of the inhaler 1. In the present embodiment, the ratchet mechanism is formed by engagement of the ramp 41 in associated steps or depressions 45 (FIG. 13) before the ramp 41 interacts with its associated ramp 42 near the fully opened position of mouthpiece cover 15. The steps or depressions 45 are preferably formed on the associated lock element 22, 23, respectively. However, other constructional solutions are possible as well.

In the present embodiment, the conveying mechanism or conveyor 5 preferably comprises the lock elements 22, 23, the axle 28 and/or the coupling element 30 in addition to the conveying wheel 14 and/or other guiding elements (not shown).

As shown in FIG. 6, the actuator 12 preferably has holes 46 that serve as inlets for enabling air to flow into the inhaler 1.

The terms "blister strip" and "blister pockets" are to be understood in a very broad sense to cover also other kinds of storage means with receptacles for the formulation.

What is claimed is:

1. Inhaler for the delivery of a powdered inhalation formulation from a finite band shaped blister strip that has a plurality of blister pockets containing doses of the inhalation formulation, comprising:
   a conveyor with a conveying wheel for producing stepwise onward movement of the blister strip,
   a mouthpiece, and
   a mouthpiece cover that is pivotable around a cover axis to open and close the mouthpiece,
   the mouthpiece cover is associated with an axle that forms the cover axis,
   the inhaler being adapted for enabling an air stream of ambient air to discharge a respective dose from an opened blister pocket and to deliver it with the ambient air as an aerosol cloud,
   wherein the mouthpiece cover is drivingly coupled with the conveyor to drive the conveying wheel and to move the blister strip onward, and
   wherein the mouthpiece cover comprises an engagement portion formed as a recess and wherein a portion of the axle engages in the recess in a manner causing the axle to rotate together with the mouthpiece cover; and wherein the portion of the axle comprises ends thereof and wherein the mouthpiece cover has wings which receive the ends of the axle.

2. Inhaler according to claim 1, wherein the recess is formed in an inside surface of the mouthpiece cover.

3. Inhaler according to claim 1, wherein the recess is formed as a blind hole.

4. Inhaler according to claim 1, wherein a portion of the axle has a shape that substantially corresponds to the recess.

5. Inhaler according to claim 4, wherein the portion of the axle comprises engagement edges or sides cooperating with or arranged in the recess.

6. Inhaler according to claim 1, further comprising an actuator which is pivotably mounted to a housing of the inhaler for rotation about an actuator axis and which is operable for causing a piercing member to puncture an aligned blister pocket, wherein the mouthpiece cover axially covers the axle or the axis of one of the actuator and the conveying wheel.

7. Inhaler according to claim 1, further comprising an actuator which is pivotably mounted to a housing of the inhaler for rotation about an actuator axis and which is operable for causing a piercing member to puncture an aligned blister pocket, wherein the actuator and the mouthpiece cover have the same opening direction.

8. Inhaler according to claim 1, wherein the mouthpiece cover is coupled with the conveying wheel via one of a transmission, a free-wheel, a slipping clutch and a lost motion coupling.

9. Inhaler according to claim 1, further comprising an actuator which is pivotably mounted to a housing of the inhaler for rotation about an actuator axis and which is operable for causing a piercing member to puncture an aligned blister pocket, wherein the actuator supports the mouthpiece.

10. Inhaler according to claim 1, further comprising an actuator which is pivotably mounted to a housing of the inhaler for rotation about an actuator axis and which is operable for causing a piercing member to puncture an aligned blister pocket, wherein the actuator has a pivot range that is at least one of smaller than a pivot range of the mouthpiece cover, and at most 20 degrees.

11. Inhaler according to claim 1, wherein said portion of the axle extends transversely relative to the axis.

12. Inhaler according to claim 11, wherein said portion of the axle is at one end thereof.

13. Inhaler according to claim 1, wherein the recess extends in a radial direction relative to said conveying wheel.

14. Inhaler according to claim 1, wherein the mouthpiece cover is connected in a manner for driving the axle.

15. Inhaler according to claim 1, wherein said portion of the axle is a wing.

16. Inhaler according to claim 1, wherein said wings have receivers that cover the ends of axle in all positions thereof.

17. Inhaler according to claim 1, wherein the recess extends transversally relative to the axis or axle.

18. Inhaler according to claim 1, wherein the recess extends radially relative to the axis or axle.

* * * * *